United States Patent
Ang et al.

(10) Patent No.: US 11,402,906 B2
(45) Date of Patent: Aug. 2, 2022

(54) SYSTEM AND METHOD FOR DETECTING EYE ACTIVITY

(71) Applicant: Agency for Science, Technology And Research, Singapore (SG)

(72) Inventors: Kai Keng Ang, Singapore (SG); Cuntai Guan, Singapore (SG)

(73) Assignee: Agency for Science, Technology and Research, Singapore (SG)

(*) Notice: Subject to any disclaimer, the term of this patent is extended or adjusted under 35 U.S.C. 154(b) by 427 days.

(21) Appl. No.: 16/498,886

(22) PCT Filed: Mar. 29, 2018

(86) PCT No.: PCT/SG2018/050160
§ 371 (c)(1),
(2) Date: Sep. 27, 2019

(87) PCT Pub. No.: WO2018/182531
PCT Pub. Date: Oct. 4, 2018

(65) Prior Publication Data
US 2021/0109592 A1    Apr. 15, 2021

(30) Foreign Application Priority Data
Mar. 31, 2017    (SG) .......................... 10201702704W

(51) Int. Cl.
*G06F 3/01*        (2006.01)
*G16H 40/67*    (2018.01)
(Continued)

(52) U.S. Cl.
CPC ............ *G06F 3/015* (2013.01); *A61B 5/1103* (2013.01); *A61B 5/291* (2021.01); *A61B 5/372* (2021.01);
(Continued)

(58) Field of Classification Search
CPC .......... G06F 3/015; G06F 3/016; G06F 3/014; G06F 3/165; G06F 3/01; G06F 3/013;
(Continued)

(56) References Cited

U.S. PATENT DOCUMENTS 6,317,627 B1 * 11/2001 Ennen .................... A61B 5/369
                                                                600/544
2012/0059273 A1    3/2012 Meggiolaro et al.
2015/0018704 A1 * 1/2015 Fang .................... A61B 5/7214
                                                                600/544

FOREIGN PATENT DOCUMENTS

CN        105700690 A     6/2016
WO    2016193979 A1    12/2016

OTHER PUBLICATIONS

Kim et al., "Artifact removal from EEG signals using the total variation method." 2015 10th Asian Control Conference (ASCC), Jun. 3, 2015, pp. 1-4 [Retrieved on Jun. 13, 2018].

(Continued)

*Primary Examiner* — Koosha Sharifi-Tafreshi
(74) *Attorney, Agent, or Firm* — Potomac Law Group, PLLC; John J. Penny, Jr.

(57) ABSTRACT

A system for detecting eye blink activity, the system including one or more processors in communication with non-transitory data storage media having instructions stored thereon that, when executed by the one or more processors configure the one or more processors to perform the steps of receiving, with a receiving module, a signal associated with eye blink activity; filtering, at a processing module, the signal to reduce noise from the signal; calculating, at the processing module, a variance of the filtered signal for estimating background noise; removing, at the processing module, background noise associated with the variance; and (Continued)

detecting, at the processing module, eye blink activity by performing duration detection.

19 Claims, 9 Drawing Sheets

(51) Int. Cl.
    *A61B 5/291*     (2021.01)
    *A61B 5/372*     (2021.01)
    *A61B 5/11*     (2006.01)
    *A61B 5/00*     (2006.01)

(52) U.S. Cl.
    CPC .............. *A61B 5/721* (2013.01); *G06F 3/013* (2013.01); *G16H 40/67* (2018.01); *A61B 5/0006* (2013.01)

(58) Field of Classification Search
    CPC ..... A61B 5/369; A61B 5/0006; A61B 5/1103; A61B 5/291; A61B 5/372; A61B 5/721; G16H 40/67
    See application file for complete search history.

(56) References Cited

OTHER PUBLICATIONS

International Search Report and Written Opinion issued in connection with corresponding International Application No. PCT/SG2018/050160 dated Jun. 29, 2018.

\* cited by examiner

SYSTEM AND METHOD FOR DETECTING EYE ACTIVITY

The present application claims priority under 35 U.S.C. § 119 to Singaporean Application No. 10201702704W filed Mar. 31, 2017, and under 35 U.S.C. § 365 to International Application No. PCT/SG2018/050160 on Mar. 29, 2018. The entire contents of these applications are incorporated by reference in their entirety.

FIELD OF THE INVENTION

The present invention relates to a system and method for detecting eye activity.

BACKGROUND OF THE INVENTION

The field of Electroencephalograhy (EEG) has been used in research for more than 100 years. In recent years, EEG has been growing rapidly, for example, in the field of Brain Computer Interfaces (BCI) to a broad range of applications.

EEG works by recording brain activity through one or more electrodes connected to a subject. However, due to the sensitivity of EEG recordings, signals received from the one or more electrodes often pick up other signals which are not associated with the brain responses. These include nearby muscle activities such as eye blinks. These signals affect the quality of the EEG signals thereby increasing noise. Therefore, artefact removal is an important part of processing EEG signals and have been extensively investigated to provide accurate EEG readings.

In addition, eye blinks or winks may be used as a trigger to indicate user instruction. For example, an eye wink may be considered a voluntary action. As such, when an eye wink is detected, the signal may be considered as a user instruction to control a certain action. This may be useful in applications such as user controls in a video game. Additional applications include controlling an unmanned aerial vehicle or drone.

Independent component analysis (ICA) is a method that can be used to remove eye blink artefacts from EEG signals. This is typically done by excluding artefacts associated with eye blink movements by excluding components associated with the artefacts in the re-mixed decomposed signal. To perform ICA, the eye blink components have to be identified from available data and many channels of EEG signals are required due to the intrinsic characteristics of the ICA algorithm. Therefore, a limitation in ICA is that it cannot be performed when only a few EEG signals are available.

Other methods that may be used to remove artefacts include filter methods that rely on peak-to-peak analysis to perform eye blink detection. However, these methods also require some data which can identify the magnitude of the peaks. These methods are typically not robust for eye blink detection, especially when other artefacts such as noise or movement artefacts are also present.

It is generally desirable to overcome or ameliorate one or more of the above described difficulties, or to at least provide a useful alternative.

SUMMARY OF THE INVENTION

In accordance with the present invention, there is provided a system for detecting eye blink activity, the system including one or more processors in communication with non-transitory data storage media having instructions stored thereon that, when executed by the one or more processors configure the one or more processors to perform the steps of:
(a) receiving, with a receiving module, a signal associated with eye blink activity;
(b) filtering, at a processing module, the signal to reduce noise from the signal;
(c) calculating, at the processing module, a variance of the filtered signal for estimating background noise;
(d) removing, at the processing module, background noise associated with the variance; and
(e) detecting, at the processing module, eye blink activity by performing duration detection.

In accordance with the present invention, there is also provided a method for detecting eye blink activity performed by one or more processors in communication with non-transitory data storage media having instructions stored thereon which, when executed by the processor or processors, performs the steps of:
(a) receiving, with a receiving module, a signal associated with eye blink activity;
(b) filtering, at a processing module, the signal to reduce noise from the signal;
(c) calculating, at the processing module, a variance of the filtered signal for estimating background noise;
(d) removing, at the processing module, background noise associated with the variance; and
(e) detecting eye blink activity, at the processing module, by performing duration detection.

In accordance with the present invention, there is also provided a method for detecting eye wink activity performed by one or more processors in communication with non-transitory data storage media having instructions stored thereon which, when executed by the processor or processors, performs the steps of:
(a) obtaining, at a processing module, data associated with a first blink activity including a first eye blink activity and a first variance associated with the first blink activity;
(b) receiving, with a receiving module, data associated with a second blink activity including a second eye blink activity and a second variance associated with the second blink activity;
(c) obtaining, at the processing module, a first number by calculating the absolute difference between the first eye blink activity and the second eye blink activity;
(d) obtaining, at the processing module, a second number by calculating the average of the square root of the first variance and the square root of the second variance multiplied by a predetermined value associated with a robustness level estimator;
(e) comparing, at the processing module, if the first number is larger than the second number; and
(f) if the first number is larger than the second number, wink activity is detected.

In accordance with the present invention, there is also provided a system for detecting eye wink activity, the system including one or more processors in communication with non-transitory data storage media having instructions stored thereon that, when executed by the one or more processors configure the one or more processors to perform the steps of:
(a) obtaining, at a processing module, data associated with a first blink activity including a first eye blink activity and a first variance associated with the first blink activity;

(b) receiving, with a receiving module, data associated with a second blink activity including a second eye blink activity and a second variance associated with the second blink activity;

(c) obtaining, at the processing module, a first number by calculating the absolute difference between the first eye blink activity and the second eye blink activity;

(d) obtaining, at the processing module, a second number by calculating the average of the square root of the first variance and the square root of the second variance multiplied by a predetermined value associated with a robustness level estimator;

(e) comparing, at the processing module, if the first number is larger than the second number; and (f) if the first number is larger than the second number, wink activity is detected.

It will be appreciated that the broad forms of the invention and their respective features can be used in conjunction, interchangeably and/or independently, and reference to separate broad forms is not intended to be limiting.

BRIEF DESCRIPTION OF THE DRAWINGS

Preferred embodiments of the invention are hereafter described, by way of non-limiting example only, with reference to the accompanying drawings, in which:

FIG. 1b is a schematic diagram of a processing module of the system of FIG. 1a;

DETAILED DESCRIPTION OF EMBODIMENTS OF THE INVENTION

Figure 1A:
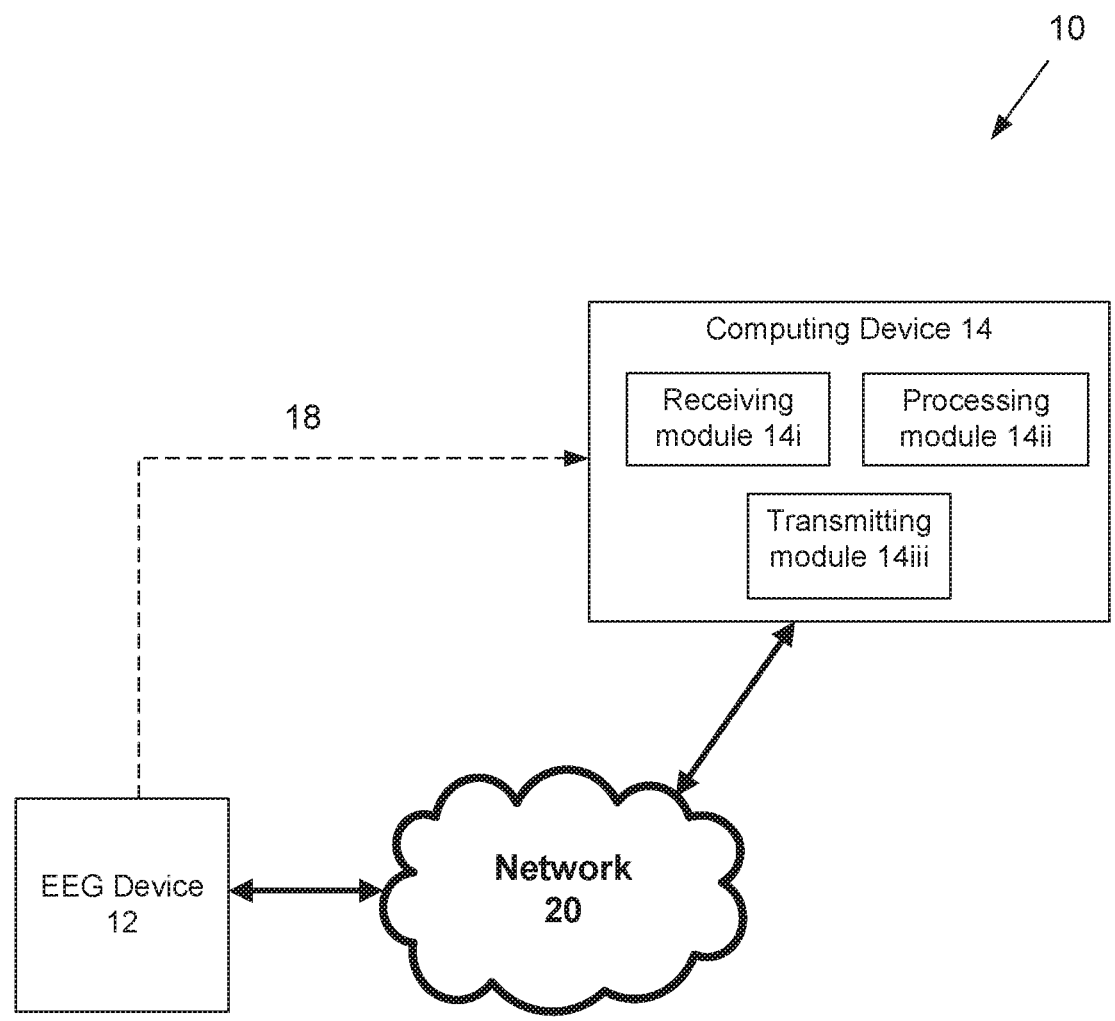
FIG. 1a is a schematic diagram of a system for detecting eye blink activity.

The system 10 shown in FIG. 1a allows eye blink activity to be detected. The system 10 includes one or more of the following:

(a) an EEG device 12; and
(b) a computing device 14.

The components of system 10 are in communication via the network 20. The communication network 20 may include the Internet, telecommunications networks and/or local area networks. Network 20 may also include wireless connections such as Bluetooth or NFC. Of course, network 20 may include wired connections such as USB or other forms of data transfer systems.

The system 10 makes detecting eye blinks and/or eye winks simpler, faster and more convenient. A minimum of 2 EEG channels are required for system 10 to work and to detect eye blinks and eye winks. The detection of eye blinks could be used to remove artefacts from EEG signals. Further analysis such as fatigue detection can also be used. The detection of eye winks could be used in Brain Computer Interfaces (BCI) applications such as a trigger to perform a certain user instruction.

System 10

As particularly shown in FIG. 1a, system 10 includes an EEG device 12, such as a BCI headband. Preferably, the EEG device 12 further includes an EEG amplifier to amplify, and convert the EEG signal. The EEG device 12 may further include a wireless module to transmit the EEG data to the computing device 14. For example, the wireless module is a Bluetooth device. In some embodiments, the EEG device 12 can also transmit the EEG data to the computing device 14 by a cabled connection 18.

The system 10 also includes a computing device 14. Computing device 14 may be embodied in the form of a mobile computing device 14a. The computing device 14 includes a receiving module 14i, a processing module 14ii and a transmitting module 14iii. The receiving module 14i is preferably configured to receive EEG data from the EEG device 12. The processing module 14ii preferably includes one or more computer processors configured to process the EEG data and detect eye blinks or eye winks.

Figure 1B:
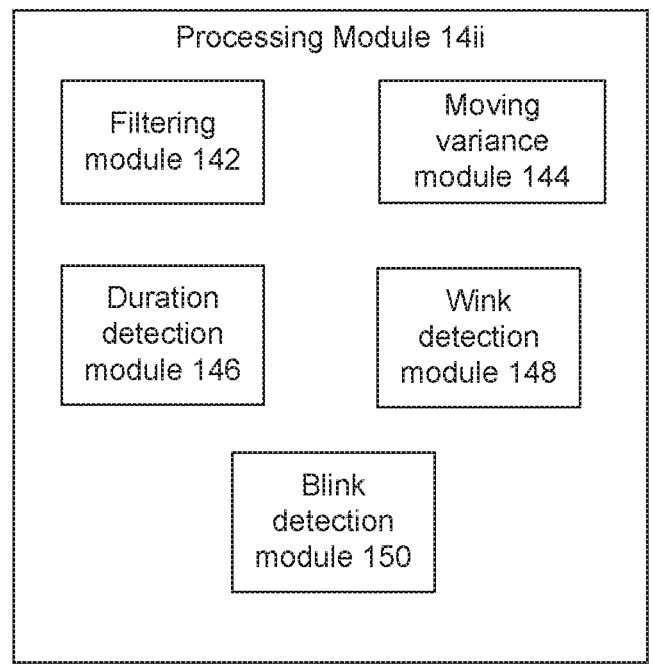

For example, the processing module 14ii of computing device 14 is configured to perform process 200 for detecting eye blinks and process 300 for detecting eye winks. As shown in FIG. 1b, for example, processing module 14ii of computing device 14 may include one or more sub-modules such as a filtering module 142, moving variance module 144, duration detection module 146, wink detection module 148 and blink detection module 150. It should be appreciated that while the above-mentioned sub-modules may be discrete components, the components can be a single or combined sub-modules configured to carry out respective tasks of the various components of the processing module 14ii.

Process for Detecting Eye Blinks 200

Figure 2:
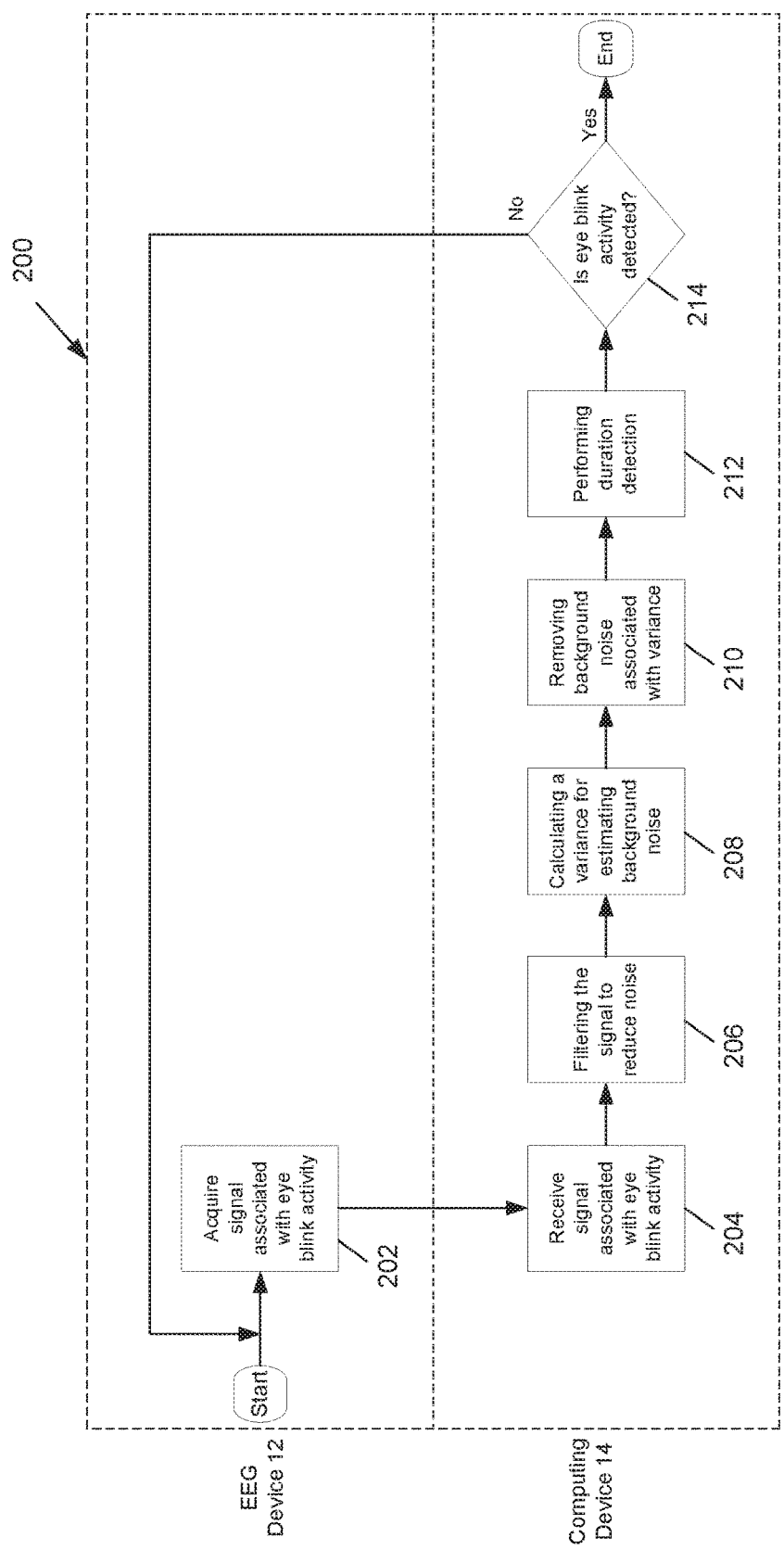
FIG. 2 is a flowchart diagram showing a process for detecting eye blink activity.

FIG. 2 particularly shows an embodiment of a process for detecting eye blinks 200. At step 202, the EEG device 12 acquires signal associated with eye blink activity. For example, the signal is acquired by one or more electrodes for receiving electroencephalography (EEG) data. Preferably, the signal received relating to eye blink activity is amplified by an amplifier to amplify and convert the EEG data acquired by the one or more electrodes before performing the step of filtering the signal.

The process 200 is performed by one or more processors in communication with non-transitory data storage media having instructions stored thereon which, when executed by the processor or processors, performs the steps of:

(a) receiving, with a receiving module 14i, a signal associated with eye blink activity (step 204);

(b) filtering, at a processing module 14ii, the signal to reduce noise from the signal (step 206);

(c) calculating, at the processing module 14ii, a variance of the filtered signal for estimating background noise (step 208);

(d) removing, at the processing module 14ii, background noise associated with the variance (step 210); and (e) detecting, at the processing module 14ii, eye blink activity by performing duration detection (step 212 and 214).

Preferably, step 204 includes the step of filtering the signal includes one or more of the following steps:

(a) applying, at the processing module 14ii, a low pass filter for removing high frequency signal associated with noise; and (b) applying, at the processing module 14*ii*, a moving average filter for reducing random noise.

For example, step 204 may be performed by the filtering module 142 of the processing module 14*ii*.

Of course other filtering methods could be used to remove parts of the signal associated with noise.

Figure 3A:
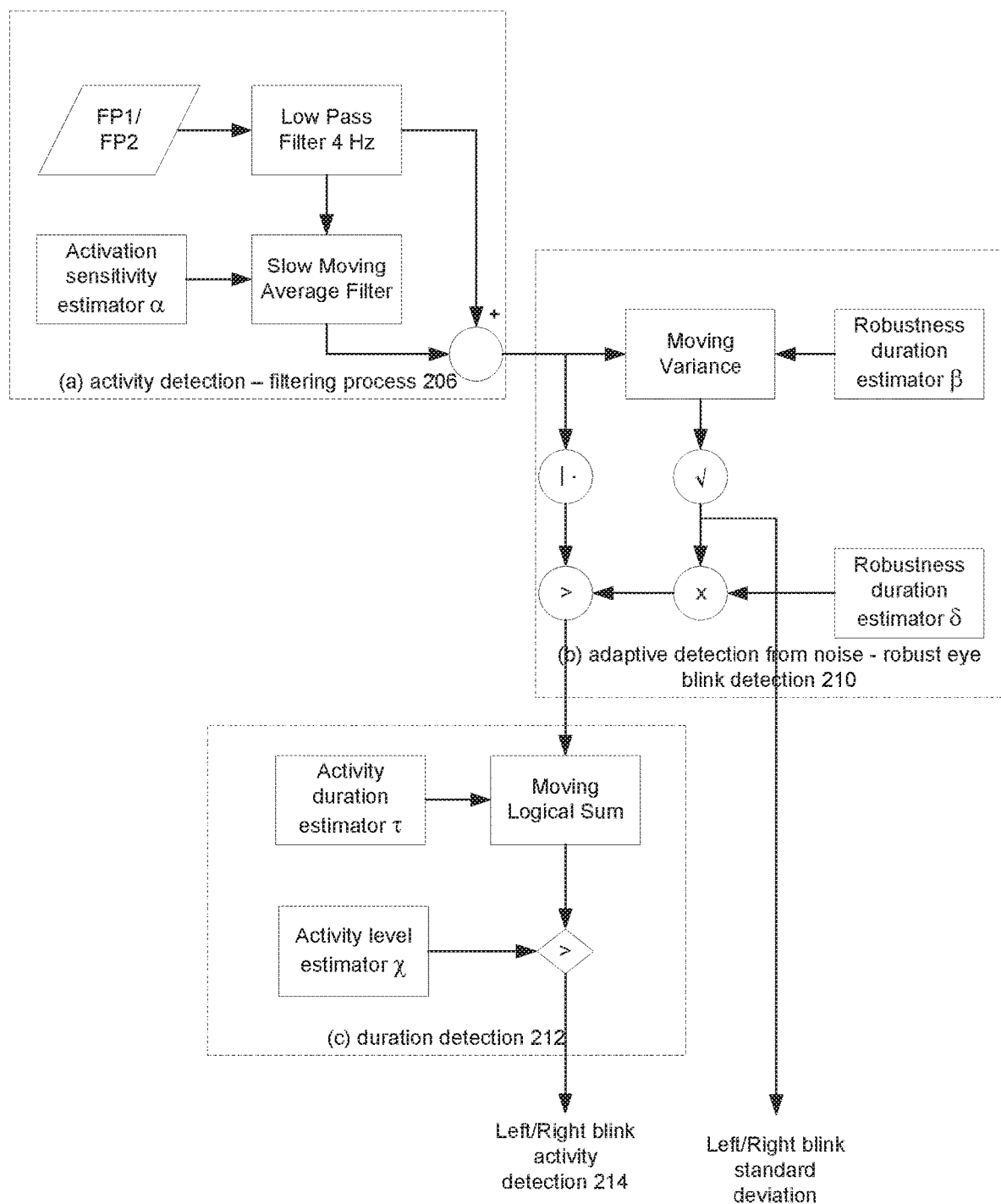
FIG. 3a is a flowchart diagram showing another exemplary process for detecting eye blink activity.

Part (a) of FIG. 3A shows an exemplary method of filtering the signal by using a 4 Hz low pass filter. Of course, a low pass filter with a different frequency could be chosen. A 4 Hz low pass filter is appropriate in some data sets as it is known that theta waves in EEG signals typically range between 4 Hz and 8 Hz and eye blink signals in EEG typically occur below 4 Hz.

Subsequently, a moving average filter is applied on the filtered signal. For example, a moving average filter is performed on the low pass filtered signal given by:

$$\tilde{X}_{FPn}(t) = \frac{1}{\alpha} \sum_{i=0}^{\alpha-1} \tilde{X}_{FPn}(t-i) \quad (1)$$

where $X_{FPn}(t)$ is the 4 Hz low pass filtered EEG of channel FPn at time instant t, n=1 or 2 for FP1 or FP2, and $\alpha$ is an activation sensitivity estimator.

For example, the value of $\alpha$ may range between 10 and 30 for a sampling frequency of 256 Hz. A lower $\alpha$ value may result in better and faster detection of eye blinks, but may also result in more false detection of eye blinks from noise. Hence, the $\alpha$ value may be selected based on experimentation as the optimum $\alpha$ value may be different for specific EEG amplifiers as their sensitivity to noise differs depending on the amplifier.

For example, the output of the blink activity detection is given by $$A_{FPn}(t)\hat{X}_{FPn}(t) - X_{FPn}(t-i) \quad (2)$$

After step 206, the signal which has been filtered is used to remove background noise associated with the variance. This may also be known as adaptive eye blink detection. In step 208, the variance for estimating background noise is calculated. In step 210, the background noise associated with the variance is removed.

For example, the step of removing background noise associated with the variance includes using a moving variance function by performing the steps of:
  (a) setting, at the processing module 14*ii*, a predetermined value to a robustness duration estimator;
  (b) setting, at the processing module 14*ii*, a predetermined value to a robustness level estimator;
  (c) calculating, at the processing module 14*ii*, the variance based on the robustness duration estimator and the filtered signal;
  (d) calculating, at the processing module 14*ii*, the square root of the variance multiplied by the robustness level estimator;
  (e) comparing, at the processing module 14*ii*, the absolute value of the filtered signal with the variance multiplied by the robustness level estimator; and
  (f) removing, at the processing module 14*ii*, background noise associated with the variance by removing signal wherein the absolute value of the filtered signal is less than the variance multiplied by the robustness level estimator.

For example, the step of removing background noise associated with the variance may be performed by the moving variance module 144 of the processing module 14*ii*.

Part (b) of FIG. 3A shows an exemplary method of adaptive detection from background noise. This process is also known as robust eye blink detection. For example, background noise from part (a) is estimated using a moving variance function given by $$\sigma^2_{FPn}(t) = \frac{1}{\beta-1}\left(\sum_{i=0}^{\beta} A^2_{FPn}(t-i) - \frac{1}{\beta}\left(\sum_{i=0}^{\beta} A_{FPn}(t-i)\right)^2\right) \quad (3)$$

where $\beta$ is robustness duration estimator.

For example, the value of $\beta$ may range from 2×256 to 10×256 for a sampling frequency of 256 Hz. A lower $\beta$ value may result in faster adaptation to changes in noise level, but a higher $\beta$ value may result in a better estimate of the noise level over a longer period of time. Therefore, the optimum $\beta$ value should be selected based on experimentation as the optimum $\beta$ value is dependent on the specific EEG amplifier used.

In other embodiments, the moving variance function may be replaced with a simple variance function, for example, which may achieve a similar result. The moving variance function only needs to perform computation on the new signal values, but a simple variance function needs to store a history of the signal values and to compute the variance using the historical signal values and the new values. Thus, the use of the moving variance function is typically more effective than the simple variance function in a real-time signal processing application.

The robust eye blink detection is then given by $$R_{FPn}(t) = |A_{FPn}(t)| > \delta\sigma_{FPn}(t) \quad (4)$$

where $R_{FPn}(t) \in \{0, 1\}$, $\delta$ is a robustness level estimator and $\sigma$ is the square root of the variance given in equation (3).

For example, the value of $\delta$ may range from 1 to 3. A lower $\delta$ value may result in a higher chance of noise being falsely detected as a blink, but a higher $\delta$ value may result in a lower chance of an actual blink being detected. The optimum $\delta$ value may be selected based on experimentation for a specific EEG amplifier. If the value of $\sigma$ is extremely high for a specific amplifier, additional upper limit to the largest value of $\sigma$ may have to be imposed to work with high noise EEG signals.

After the background noise associated with the variance is removed, duration detection is performed at step 212. For example, the step of performing duration detection includes the steps of:
  (a) setting, at the processing module 14*ii*, a predetermined number to an activity level estimator for estimating the activity level of a typical blink activity;
  (b) obtaining, at the processing module 14*ii*, a first number by calculating the sum of the signal, after the step of filtering and removing the background noise associated with the variance, from time is zero to time is a predetermined number associated with an activity duration estimator; and
  (c) detecting, at the processing module 14*ii*, eye blink activity by:
    (i) comparing if the first number is larger than the activity level estimator; and
    (ii) if the first number is larger than the activity level estimator, blink activity is detected.

For example, step 212 may be performed by the duration detection module 146 of the processing module 14*ii*. For example, step (c) of step 212 may be performed by the wink detection module 148 of the processing module 14*ii*.

Part (c) of FIG. 3A shows an exemplary eye blink duration detection process. For example, $$B_L(t) = \left(\sum_{i=0}^{\tau} \sigma_{FP1}(t) > \chi\right) \quad (5)$$

$$B_R(t) = \left(\sum_{i=0}^{\tau} \sigma_{FP2}(t) > \chi\right) \quad (6)$$

where blinks left $B_L(t) \in \{0, 1\}$, blinks right $B_R(t) \in \{0, 1\}$, $\tau$ is an activity duration estimator, and $\chi$ is a activity level estimator.

The value of $\delta$ sets the window of detection for an eye blink. For example, a value of 25 for a sample frequency of 256 Hz configures the system to detect eye blinks for a period of about 0.1 s. Together with the use of the parameter $\chi$, different durations of eye blinks can be detected. If the minimum duration of an eye blink to be detected is 0.05 s, then can be set to a value of 12, for example. If the duration of the eye blinks does not matter, then $\chi$ can be set to the value 1, for example. Generally, the value of $\delta$ should be greater than the value of $\chi$.

Figure 3B:
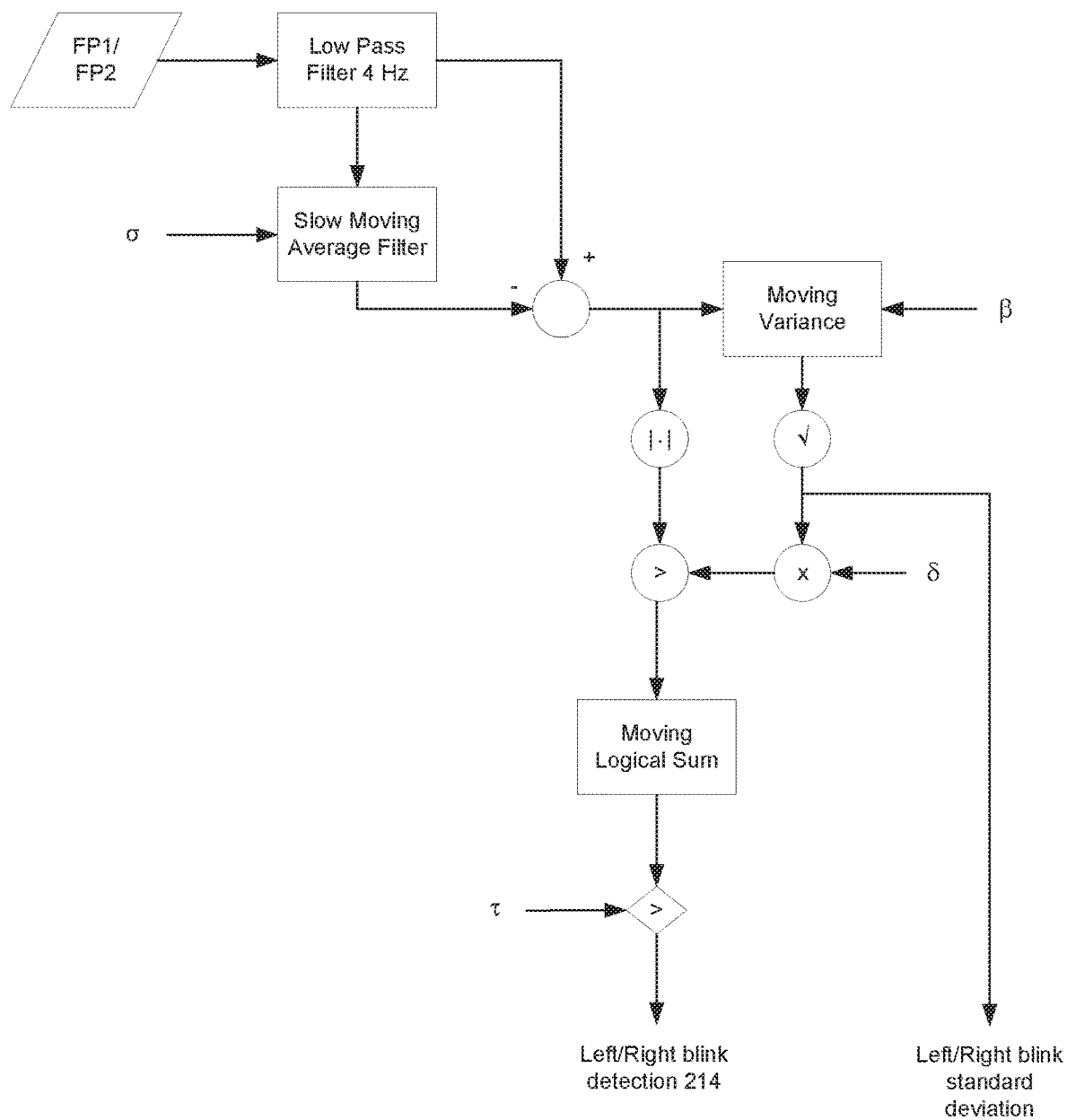
FIG. 3b is a flowchart diagram showing another exemplary process for detecting eye blink activity.

FIG. 3B shows another exemplary process 200 for detecting left or right blinks and for obtaining left or right blink standard deviation.

Process for Detecting Eye Winks 400

After the step of detecting eye blinks, process for detecting eye winks 400 may be performed. The process for detecting eye winks 400 may use eye blink detected by any method.

Figure 4:
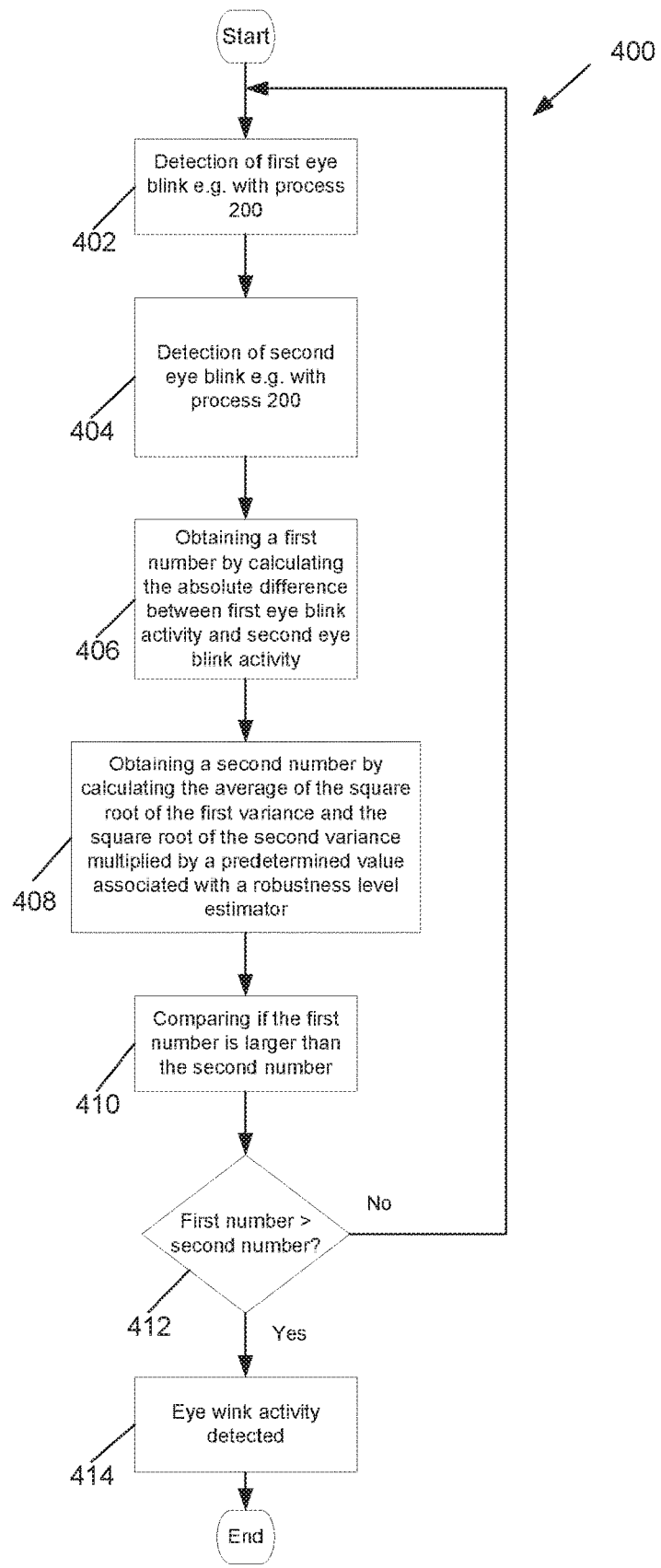
FIG. 4 is a flowchart diagram showing a process for detecting eye blink activity.

For example, as particularly shown in FIG. 4, the method for detecting wink activity further includes the steps of:
(a) receiving, with the receiving module, a second signal relating to a second eye blink activity;
(b) filtering, at the processing module 14ii, the second signal to reduce noise from the second signal;
(c) calculating, at the processing module 14ii, a second variance of the second filtered signal for estimating background noise;
(d) removing, at the processing module 14ii, background noise associate with the second variance;
(e) detecting, at the processing module 14ii, a second eye blink activity by performing duration detection; and
(f) detecting, at the processing module 14ii, wink activity by:
 (i) obtaining a first number by calculating the absolute difference between the first eye blink activity and the second eye blink activity (step 408);
 (ii) obtaining a second number by calculating the average of the square root of the first variance and the square root of the second variance multiplied by a predetermined value associated with a robustness level estimator (step 410);
 (iii) comparing if the first number is larger than the second number (step 412);
 (iv) if the first number is larger than the second number, wink activity is detected (step 414).

For example, steps 408, 410 and 412 may be performed by the wink detection module 150 of the processing module 14ii.

Figure 5A:
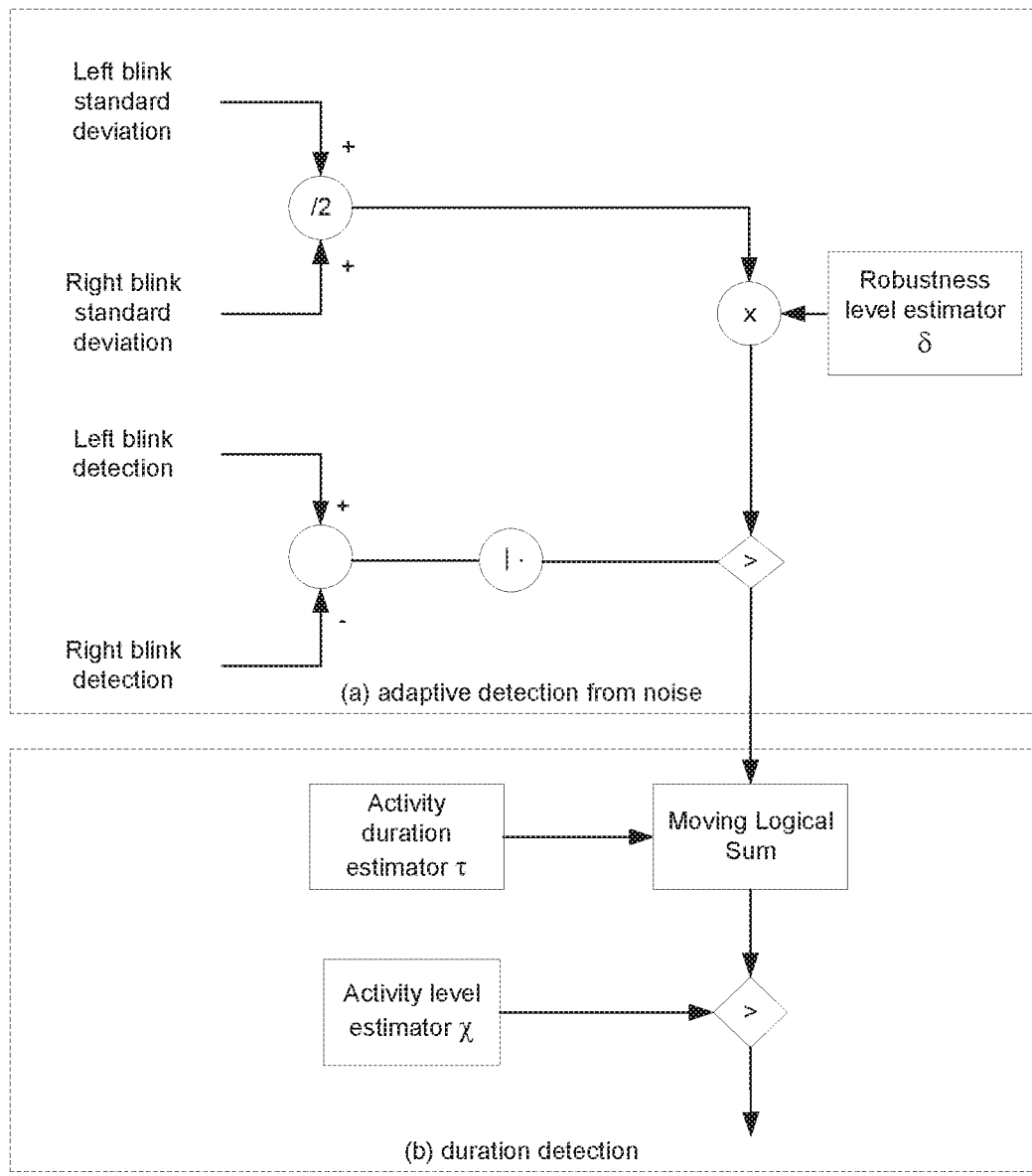
FIG. 5a is a flowchart diagram showing another exemplary process for detecting eye blink activity.
Figure 5B:
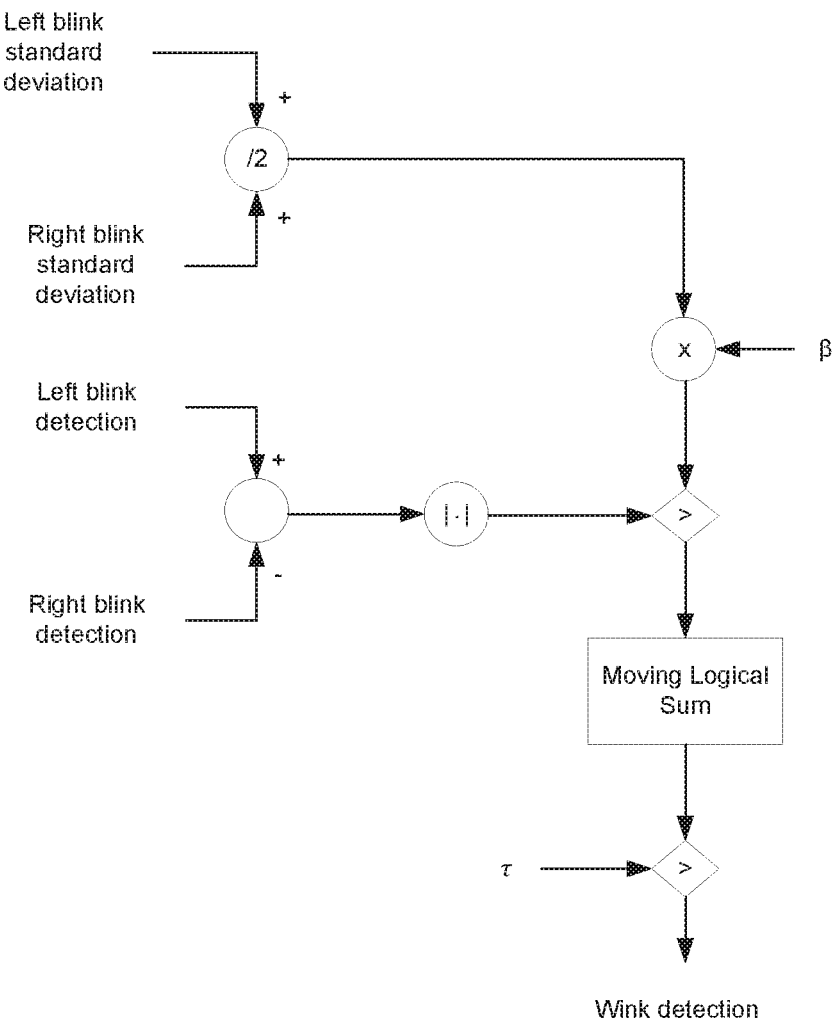
FIG. 5b is a flowchart diagram showing another exemplary process for detecting eye blink activity.

For example, FIG. 5a shows an example of performing process 400. As shown in FIG. 5a, the process includes part (a) adaptive detection from noise and part (b) duration detection. For example, part (a) comprises robust wink activity detection given by:

$$Y(t) = \left(|B_L(t) - B_R(t)| > \delta \frac{(\sigma_{FP1}(t) + \sigma_{FP2}(t))}{2}\right) \quad (7)$$

where $Y(t) \in \{0, 1\}$, $\sigma_{FP1}$ and $\sigma_{FP2}$ are the standard deviations given by equation (3), and $\delta$ is the robustness level estimator used in equation (4).

After part (a) is performed, part (b) is performed. For example, part (b) comprises adaptive wink duration detection from background blinks given by:

$$W(t) = \left(\sum_{i=0}^{t} Y(t) > \chi\right) \quad (8)$$

where $W(t) \in \{0, 1\}$, $\tau$ is an activity duration estimator and x is a activity level estimator used in equations (5) and (6).

FIG. 3B shows another example of process 400.

Advantageously, the process 200 and 400 provide methods for detecting eye blinks and/or winks from a minimum of 2 EEG signals recorded from the prefrontal cortex, for example. Typically, EEG data from dry EEG amplifiers are noisy and may be highly susceptible to false detection of eye blink or eye wink activity, especially in the presence of noisy EEG data. Process 200 and 400 provide a method which may detect an eye blink and/or eye wink by constantly monitoring the variance of the EEG data to eliminate background noise and by incorporating a duration detection step to eliminating enhanced filtered signals which are shorter than a predetermined interval.

For example, the method for detecting voluntary eye blinks and/or winks can be applied to a computer or electronic game, where a user wearing a wireless BCI, controls a game controller, wherein specific controls are assigned to blinks and winks. For example, in a first person shooting game, wearing the BCI headband would ready a weapon, working alongside a joystick controller or controllers to manipulate or move the weapon, the weapon will fire upon detecting a wink from the user.

Mobile Computer Device 14a

It is contemplated that process 200 and 400 could be performed on a computing device such as a mobile computer device 14a. Advantageously, the process 200 and 400 do not need to be performed on a resource hungry computing device with large amounts of computing power. Of course it would be possible to perform process 200 and 400 on any computing device 14 such as a server.

Figure 6:
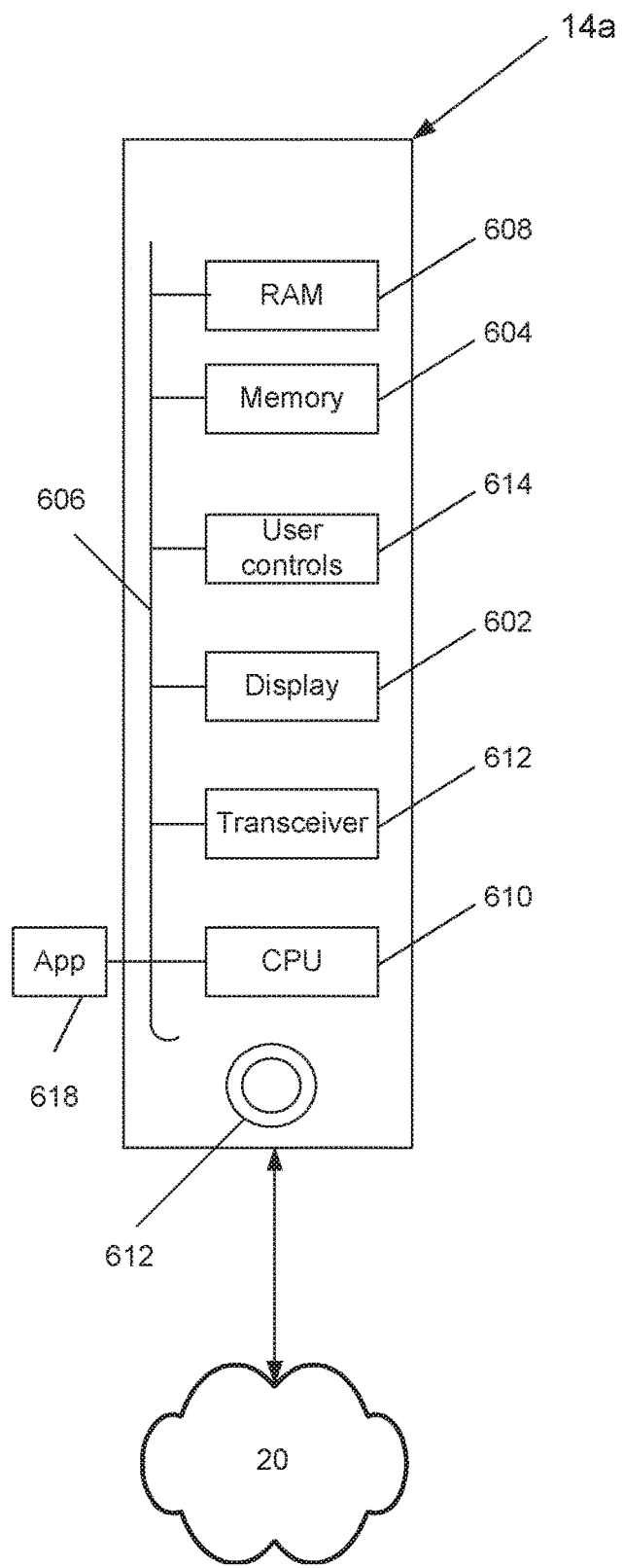
FIG. 6 is a schematic diagram showing components of an exemplary mobile computing device.

FIG. 6 is a block diagram showing an exemplary mobile computer device 14a in which embodiments of the invention may be practiced. The mobile computer device 14a may be a mobile computer device such as a smart phone, a wearable device, a palm-top computer, and multimedia Internet enabled cellular telephones. For ease of description, the mobile computer device 14a is described below, by way of non-limiting example, with reference to a mobile device in the form of an iPhone™ manufactured by Apple™, Inc or one manufactured by LG™, HTC™ and Samsung™, for example.

As shown, the mobile computer device 14a includes the following components in electronic communication via a bus 606:
(a) a display 602;
(b) non-volatile (non-transitory) memory 604;
(c) random access memory ("RAM") 608;
(d) N processing components 610;

(e) a transceiver component 612 that includes N transceivers; and (f) user controls 614.

The receiving module 14*i* and transmitting module 14*iii* of computing device 14 may be performed by the transceiver component 612 of mobile computer device 14*a*, for example. The processing module 14*ii* of computing device 14 may be performed by the N processing components 610 of mobile computer device 14*a*, for example.

Each of the steps of the process, for example process 300 and/or 400, performed by the computing system 14, may be executed by a module, such as receiving module 14*i*, processing module 14*ii* or transmitting module 14*iii*, or portion of a module, such as filtering module 142, moving variance module 144, duration detection module 146, wink detection module 148 and blink detection module 150. The processes may be embodied in a non-transient machine readable and/or computer-readable medium for configuring a computer system to execute the method. The software modules may be stored within and/or transmitted to a computer system memory to configure the computer system to perform functions of the module.

Although the components depicted in FIG. 6 represent physical components, FIG. 6 is not intended to be a hardware diagram. Thus, many of the components depicted in FIG. 6 may be realized by common constructs or distributed among additional physical components. Moreover, it is certainly contemplated that other existing and yet-to-be developed physical components and architectures may be utilized to implement the functional components described with reference to FIG. 6.

The display 602 generally operates to provide a presentation of content to a user, and may be realized by any of a variety of displays (e.g., CRT, LCD, HDMI, micro-projector and OLED displays).

In general, the non-volatile data storage 604 (also referred to as non-volatile memory) functions to store (e.g., persistently store) data and executable code.

In some embodiments for example, the non-volatile memory 604 includes bootloader code, modem software, operating system code, file system code, and code to facilitate the implementation components, well known to those of ordinary skill in the art, which are not depicted nor described for simplicity.

In many implementations, the non-volatile memory 604 is realized by flash memory (e.g., NAND or ONENAND memory), but it is certainly contemplated that other memory types may be utilized as well. Although it may be possible to execute the code from the non-volatile memory 604, the executable code in the non-volatile memory 604 is typically loaded into RAM 608 and executed by one or more of the N processing components 610.

The N processing components 610 in connection with RAM 608 generally operate to execute the instructions stored in non-volatile memory 604. As one of ordinarily skill in the art will appreciate, the N processing components 610 may include a video processor, modem processor, DSP, graphics processing unit (GPU), and other processing components.

The transceiver component 612 includes N transceiver chains, which may be used for communicating with external devices via wireless networks. Each of the N transceiver chains may represent a transceiver associated with a particular communication scheme. For example, each transceiver may correspond to protocols that are specific to local area networks, cellular networks (e.g., a CDMA network, a GPRS network, a UMTS networks), and other types of communication networks.

It should be recognized that FIG. 6 is merely exemplary and in one or more exemplary embodiments, the functions described herein may be implemented in hardware, software, firmware, or any combination thereof. If implemented in software, the functions may be stored on or transmitted over as one or more instructions or code encoded on a non-transitory computer-readable medium 604. Non-transitory computer-readable medium 604 includes both computer storage medium and communication medium including any medium that facilitates transfer of a computer program from one place to another. A storage medium may be any available medium that can be accessed by a computer.

Throughout this specification, unless the context requires otherwise, the word "comprise", and variations such as "comprises" and "comprising", will be understood to imply the inclusion of a stated integer or step or group of integers or steps but not the exclusion of any other integer or step or group of integers or steps.

The reference to any prior art in this specification is not, and should not be taken as, an acknowledgment or any form of suggestion that the prior art forms part of the common general knowledge.

The invention claimed is:

1. A system for detecting eye blink activity, the system including one or more processors in communication with non-transitory data storage media having instructions stored thereon that, when executed by the one or more processors configure the one or more processors to perform the steps of:
   (a) receiving, with a receiving module, a signal associated with eye blink activity;
   (b) filtering, at a processing module, the signal to reduce noise from the signal;
   (c) calculating, at the processing module, a variance of the filtered signal for estimating background noise;
   (d) removing, at the processing module, background noise associated with the variance; and
   (e) detecting, at the processing module, eye blink activity by performing duration detection.

2. The system claimed in claim 1, wherein the step of removing background noise associated with the variance includes using a moving variance function, wherein the system is further configured to perform the steps of:
   (a) setting, at the processing module, a predetermined value to a robustness duration estimator;
   (b) setting, at the processing module, a predetermined value to a robustness level estimator;
   (c) calculating, at the processing module, the variance based on the robustness duration estimator and the filtered signal;
   (d) calculating, at the processing module, the square root of the variance multiplied by the robustness level estimator;
   (e) comparing, at the processing module, the absolute value of the filtered signal with the variance multiplied by the robustness level estimator; and
   (f) removing, at the processing module, background noise associated with the variance by removing signal wherein the absolute value of the filtered signal is less than the variance multiplied by the robustness level estimator.

3. The system claimed in claim 1, wherein the step of performing duration detection includes the system being further configured to perform the steps of:

(a) setting, at the processing module, a predetermined number to an activity level estimator for estimating the activity level of a typical blink activity;
(b) obtaining, at the processing module, a first number by calculating the sum of the signal, after the step of filtering and removing the background noise associated with the variance, from time is zero to time is a predetermined number associated with an activity duration estimator; and
(c) detecting, at the processing module, eye blink activity by:
(i) comparing if the first number is larger than the activity level estimator; and
(ii) if the first number is larger than the activity level estimator, blink activity is detected.

4. The system claimed in claim 1, wherein the step of filtering the signal includes the system being further configured to perform one or more of the following steps:
(a) applying, at the processing module, a low pass filter for removing high frequency signal associated with noise; and
(b) applying, at the processing module, a moving average filter for reducing random noise.

5. The system claimed in claim 1, wherein the system further includes one or more electrodes for receiving electroencephalography (EEG) data configured to receive signal associated with eye blink activity.

6. The system claimed in claim 5, wherein the system further includes an amplifier to amplify and convert the EEG data acquired by the one or more electrodes before performing the step of filtering the signal.

7. The system claimed in claim 1, wherein the system is further configured to detect wink activity by performing the steps of:
(a) receiving, with the receiving module, a second signal relating to a second eye blink activity;
(b) filtering, at the processing module, the second signal to reduce noise from the second signal;
(c) calculating, at the processing module, a second variance of the second filtered signal for estimating background noise;
(d) removing, at the processing module, background noise associate with the second variance;
(e) detecting a second eye blink activity, at the processing module, by performing duration detection; and
(f) detecting wink activity, at the processing module, by:
(i) obtaining a first number by calculating the absolute difference between the first eye blink activity and the second eye blink activity;
(ii) obtaining a second number by calculating the average of the square root of the first variance and the square root of the second variance multiplied by a predetermined value associated with a robustness level estimator;
(iii) comparing if the first number is larger than the second number; and
(iv) if the first number is larger than the second number, wink activity is detected.

8. A method for detecting eye blink activity performed by one or more processors in communication with non-transitory data storage media having instructions stored thereon which, when executed by the processor or processors, performs the steps of:
(a) receiving, with a receiving module, a signal associated with eye blink activity;
(b) filtering, at a processing module, the signal to reduce noise from the signal;
(c) calculating, at the processing module, a variance of the filtered signal for estimating background noise;
(d) removing, at the processing module, background noise associated with the variance; and
(e) detecting eye blink activity, at the processing module, by performing duration detection.

9. The method claimed in claim 8, wherein the step of removing background noise associated with the variance includes using a moving variance function by performing the steps of:
(a) setting, at the processing module, a predetermined value to a robustness duration estimator;
(b) setting, at the processing module, a predetermined value to a robustness level estimator;
(c) calculating, at the processing module, the variance based on the robustness duration estimator and the filtered signal;
(d) calculating, at the processing module, the square root of the variance multiplied by the robustness level estimator;
(e) comparing, at the processing module, the absolute value of the filtered signal with the variance multiplied by the robustness level estimator; and
(f) removing, at the processing module, background noise associated with the variance by removing signal wherein the absolute value of the filtered signal is less than the variance multiplied by the robustness level estimator.

10. The method claimed in claim 8, wherein the step of performing duration detection includes the steps of:
(a) setting, at the processing module, a predetermined number to an activity level estimator for estimating the activity level of a typical blink activity;
(b) obtaining, at the processing module, a first number by calculating the sum of the signal, after the step of filtering and removing the background noise associated with the variance, from time is zero to time is a predetermined number associated with an activity duration estimator; and
(c) detecting eye blink activity, at the processing module, by:
(i) comparing if the first number is larger than the activity level estimator; and
(ii) if the first number is larger than the activity level estimator, blink activity is detected.

11. The method claimed in claim 8, wherein the step of filtering the signal includes one or more of the following steps:
(a) applying a low pass filter, at the processing module, for removing high frequency signal associated with noise; and
(b) applying a moving average filter, at the processing module, for reducing random noise.

12. The method claimed in claim 8, wherein the signal received associated with eye blink activity is acquired by one or more electrodes for receiving electroencephalography (EEG) data.

13. The method claimed in claim 12, wherein the signal received relating to eye blink activity is amplified by an amplifier to amplify and convert the EEG data acquired by the one or more electrodes before performing the step of filtering the signal.

14. The method claimed in claim 8, wherein the method for detecting wink activity further includes the steps of:
(a) receiving, with the receiving module, a second signal relating to a second eye blink activity;

(b) filtering, at the processing module, the second signal to reduce noise from the second signal;
(c) calculating, at the processing module, a second variance of the second filtered signal for estimating background noise;
(d) removing background noise, at the processing module, associate with the second variance;
(e) detecting a second eye blink activity, at the processing module, by performing duration detection; and
(f) detecting wink activity, at the processing module, by:
  (i) obtaining a first number by calculating the absolute difference between the first eye blink activity and the second eye blink activity;
  (ii) obtaining a second number by calculating the average of the square root of the first variance and the square root of the second variance multiplied by a predetermined value associated with a robustness level estimator;
  (iii) comparing if the first number is larger than the second number; and
  (iv) if the first number is larger than the second number, wink activity is detected.

15. A method for detecting eye wink activity performed by one or more processors in communication with non-transitory data storage media having instructions stored thereon which, when executed by the processor or processors, performs the steps of:
  (a) obtaining, at a processing module, data associated with a first blink activity including a first eye blink activity and a first variance associated with the first blink activity;
  (b) receiving, with a receiving module, data associated with a second blink activity including a second eye blink activity and a second variance associated with the second blink activity;
  (c) obtaining, at the processing module, a first number by calculating the absolute difference between the first eye blink activity and the second eye blink activity;
  (d) obtaining, at the processing module, a second number by calculating the average of the square root of the first variance and the square root of the second variance multiplied by a predetermined value associated with a robustness level estimator;
  (e) comparing, at the processing module, if the first number is larger than the second number; and
  (f) if the first number is larger than the second number, wink activity is detected.

16. The method of claim 15 wherein the data associated with a first and second blink activity was obtained by the one or more processors performing the steps of:
  (a) receiving, with the receiving module, a signal associated with eye blink activity;
  (b) filtering, at the processing module, the signal to reduce noise from the signal;
  (c) calculating, at the processing module, a variance of the filtered signal for estimating background noise;
  (d) removing, at the processing module, background noise associated with the variance; and
  (e) detecting, at the processing module, eye blink activity by performing duration detection.

17. The method claimed in claim 15, wherein the step of removing background noise associated with the variance includes using a moving variance function by performing the steps of:
  (a) setting, at the processing module, a predetermined value to a robustness duration estimator;
  (b) setting, at the processing module, a predetermined value to a robustness level estimator;
  (c) calculating, at the processing module, the variance based on the robustness duration estimator and the filtered signal;
  (d) calculating, at the processing module, the square root of the variance multiplied by the robustness level estimator;
  (e) comparing, at the processing module, the absolute value of the filtered signal with the variance multiplied by the robustness level estimator; and
  (f) removing, at the processing module, background noise associated with the variance by removing signal wherein the absolute value of the filtered signal is less than the variance multiplied by the robustness level estimator.

18. A system for detecting eye wink activity, the system including one or more processors in communication with non-transitory data storage media having instructions stored thereon that, when executed by the one or more processors configure the one or more processors to perform the steps of:
  (a) obtaining, at a processing module, data associated with a first blink activity including a first eye blink activity and a first variance associated with the first blink activity;
  (b) receiving, with a receiving module, data associated with a second blink activity including a second eye blink activity and a second variance associated with the second blink activity;
  (c) obtaining, at the processing module, a first number by calculating the absolute difference between the first eye blink activity and the second eye blink activity;
  (d) obtaining, at the processing module, a second number by calculating the average of the square root of the first variance and the square root of the second variance multiplied by a predetermined value associated with a robustness level estimator;
  (e) comparing, at the processing module, if the first number is larger than the second number; and
  (f) if the first number is larger than the second number, wink activity is detected.

19. The system of claim 18, wherein the data associated with a first and second blink activity was obtained by the one or more processors performing the steps of:
  (a) receiving, with the receiving module, a signal associated with eye blink activity;
  (b) filtering, at the processing module, the signal to reduce noise from the signal;
  (c) calculating, at the processing module, a variance of the filtered signal for estimating background noise;
  (d) removing, at the processing module, background noise associated with the variance; and
  (e) detecting, at the processing module, eye blink activity by performing duration detection.

* * * * *